United States Patent [19]

Rodler

[11] 4,270,545

[45] Jun. 2, 1981

[54] APPARATUS FOR EXAMINING BIOLOGICAL BODIES WITH ELECTROMAGNETIC FIELDS

[76] Inventor: Hans Rodler, Pehamweg 3-5, Graz-Neuhart, Austria

[21] Appl. No.: 940,990

[22] Filed: Sep. 11, 1978

Related U.S. Application Data

[63] Continuation-in-part of Ser. No. 787,974, Apr. 15, 1977, abandoned.

[30] Foreign Application Priority Data

Apr. 20, 1976 [AT] Austria ................................ 2874/76

[51] Int. Cl.$^3$ ............................................... A61B 5/05
[52] U.S. Cl. .................................................. 128/653
[58] Field of Search ........ 128/630, 653, 690, 693–694, 128/721, 734; 324/0.5 A, 0.5 AC, 0.5 AH, 0.5 MA, 239–243, 71 R

[56] References Cited

U.S. PATENT DOCUMENTS

| | | | |
|---|---|---|---|
| 2,451,596 | 10/1948 | Wheeler ................................ 324/243 |
| 3,060,371 | 10/1962 | Townsend et al. ............... 324/0.5 A |
| 3,443,209 | 5/1969 | Nelson et al. ..................... 324/0.5 H |
| 3,564,398 | 2/1971 | Nelson .............................. 324/0.5 H |
| 3,731,184 | 5/1973 | Goldberg et al. ..................... 324/239 |
| 3,789,832 | 2/1974 | Damadian ......................... 324/0.5 A |
| 3,789,834 | 2/1974 | Duroux .............................. 128/653 |
| 3,882,374 | 5/1975 | McDaniel ............................ 324/243 |
| 3,980,076 | 9/1976 | Wikswo, Jr. et al. ............... 128/653 |
| 4,015,196 | 3/1977 | Moore et al. ..................... 324/0.5 A |
| 4,095,180 | 6/1978 | Brown ................................. 324/243 |

OTHER PUBLICATIONS

Tarjan, Peter P. et al., "Electrodeless Measurement of the Effective Resistivity of the Human Torso & Head by Mag. Indeta," IEEE BME Trans., vol. 15; No. 4, Oct. 1968, pp. 266–278.

*Primary Examiner*—Robert W. Michell
*Assistant Examiner*—Francis J. Jaworski
*Attorney, Agent, or Firm*—Kurt Kelman

[57] ABSTRACT

The primary field generated by a transmitting loop or coil energized with a AC current induces secondary currents within the body which in turn generate a secondary field. The secondary field is picked up by a pick-up loop or coil. A compensation coil is energized so that no voltage is induced in the pick-up coil when a reference body having the same resistivity is substituted for the body in which measurement are to be carried out. To compensate for body movements, the primary field can have a lower and a high freqency component. Since the high frequency components penetrate the body only to a predetermined depth (or not at all) the difference between the picked-up high or low frequencies signals is substantially independent of the distance between the object being measured and the measuring apparatus. Sectional views of larger areas of the body are generated by scanning sequentially with a plurality of transmitters spaced from each other and energized with phase-shifted currents and display of the corresponding picked-up signals on a cathode ray tube.

6 Claims, 15 Drawing Figures

APPARATUS FOR EXAMINING BIOLOGICAL BODIES WITH ELECTROMAGNETIC FIELDS

This is a continuation-in-part of my application Ser. No. 787,974, filed Apr. 15, 1977, now abandoned.

BACKGROUND OF THE INVENTION

The present invention relates to apparatus for examining, measuring and recording physiologic processes in biological bodies or parts of bodies by use of electromagnetic fields. Specifically, the body or parts of the body are exposed to electromagnetic alternating fields generated by a transmitting device and the resulting magnetic phenomena in the body are measured at its surface.

Measuring apparatus for the examination of physiological processes in biological objects was already proposed in German Auslegeschrift No. 2,255,757. In this publication, apparatus was disclosed in which the processes were to be identified and measured by measurement of the electromagnetic as well as the electrical component of the primary field. However, the measurement of these two components cannot yield adequate results, since in order to do so both of the field strengths must relate to the same enclosed space. If they do not relate to the same space they cannot be put into a mathematical relationship to each other, as is required if the impedance of the space is to be calculated.

Further, in known apparatus the distance between the object to be measured and the measuring system may affect the measuring results to a greater extent than do the physiological processes in the body. Movement of the body also distorts the result and can mask the changes resulting from physiological causes. It must also be considered that physiological processes internal to the body cause changes in the order of 1/1000 of the effective resistance of the body, thereby having only little influence on the primary field. The primary field does not vary greatly as a function of the impedance of the body, since the resistance to radiation of the proposed arrangement is relatively low ohmic.

SUMMARY OF THE INVENTION

It is an object of the present invention to furnish apparatus which allows physiological processes whose effect lies under 1/100th or even 1/1000th of the body's impedance to be determined.

The present invention relates to apparatus for measuring physiological processes in a biological body. It comprises transmitting means for generating a primary electromagnetic field adapted to induce currents in the body, said current creating a secondary field. Pick-up means are provided which are coupled to said secondary field for furnishing measurement signals indicative of the value of a predetermined characteristic of said secondary field but substantially independent of said primary field. The pick-up means comprises display means for furnishing a display of the measurement signals.

In a preferred embodiment of the present invention the pick-up means comprises at least one pick-up element arranged in said primary and secondary fields in such a manner that measurement signals furnished thereby are substantially independent of said primary field.

In a further preferred embodiment, said pick-up means comprises a pick-up element for furnishing pick-up signals having a first component resulting from said primary and a second component resulting from said secondary electromagnetic field, a compensation element arranged relative to said pick-up element and said transmitting means so that it furnishes compensation signals adapted to cancel said first component of said pick-up signals, and circuit means connected to said pick-up element and said compensation element for furnishing said measurement signals in response to said pick-up signals and said compensation signals.

In a preferred embodiment of the invention said primary electromagnetic field has a reference phase angle and said pick-up means comprises a pick-up coil furnishing pick-up signals and having an electromagnetic axis. Means are provided for adjusting the angle between said reference phase angle and said electromagnetic axis until two equally large primary field components canceling each other are created in said pick-up coil, whereby said pick-up signals vary as a function of said secondary field only.

In all embodiments of the present invention, the effects of the primary, that is of the exciting field, are suppressed or compensated for and do not appear in the displayed measurement results. Only the effects of the secondary field, that is the field generated by the secondary currents induced in the object by the primary electromagnetic field are considered. The latter have a much closer relationship to the impedances within the body and can be modulated by the physiological processes to an extent that can be measured. In one embodiment, regulating means are provided which are adjusted by compensating fully for the primary electromagnetic field in a homogenous comparison body and transferring the full compensation to the body to be measured, whereby differences between the compensation values and the picked-up values constitute the desired measurement signals. Rhythmic physiological processes as, for example, circulatory changes, breathing and flow processes may be monitored. In a preferred embodiment of the invention, the transmitting means comprises a plurality of transmitting elements, and energizing means for energizing each of said transmitting elements at a frequency different from the other transmitting elements. By thus generating a primary field with different frequencies, frequency-dependent physiological processes are monitored. This is particularly useful for measuring processes within the interior of the biological body, since the induced secondary current and thereby also the secondary field have a direct relationship with the resistivity $\rho$. Since $(\rho)$ is a pure material constant, this unit includes all physiological processes.

Both the magnitude of the secondary field and the direction of the secondary field vector can be determined in a further embodiment of the present invention wherein the pick-up means comprises a first and second pick-up element arranged at 90° to each other, the pick-up elements having an electromagnetic axis. In this embodiment the pick-up means further comprises means for rotating said pick-up elements in such a manner as to rotate said electromagnetic axis thereof relative to the reference angle of said primary electromagnetic field until said measurement signal is substantially independent of the latter. Measurement means are provided which are interconnected between said first and second pick-up element and said display means, for furnishing amplitude and phase angle signals in response to signals furnished by said first and second pick-up elements.

In another embodiment three or more transmitting elements are arranged along the circumference of a circle, with the axes positioned radially or axially, while the exciting currents delivered by the oscillator are phase-shifted in the transmitting elements in accordance with the angular distribution of the latter, so that a rotating field results. The pick-up elements comprise one or more crossed spool arrangements, whose axes are arranged at an angle to the primary field for compensation thereof, the pick-up elements being connected to measuring and evaluating devices for determining the phase and amplitude. Since a rotating field, as is well known, flows through the object with differing field directions and different angles, the picked up secondary field can be indentified in correspondence to its phase position with the biological happenings which lie in the direction of the current thereby new criteria for the evaluation has been developed.

In accordance with the present invention, the phase position of the transmitting elements is mutually adjustable, so that measurements can be carried out in preferred directions. The superimposed phase position is herein utilized as a criterion of the direction, this phase position also being automatically controllable by a corresponding device.

In accordance with the invention, the object to be measured is positioned between the transmitting element and the pick-up element.

Since an abundance of information is hidden in the so-derived measuring voltages, it is practical to store the latter and, from the relationship among a plurality of components and measuring values derived from different angles, compute the desired values and display the same in topographical representation.

Thus in accordance with the present invention for topographic evaluation and storage, XY position pick-offs are arranged on the movable pick-up elements, the picked-up measured values of the latter controlling the graphic plotting device and computer device with respect to position. Storage devices are provided for storage of the measuring signal and the position signal.

By suitable programming of the computer, it is possible to generate a display of circulatory processes, since blood has the characteristic of changing resistivity with increasing velocity. Observation of the circulatory processes is thus made possible without interference and above all over longer time periods. Many metabolic processes which are otherwise only derivable by means of isotope methods, that is with a radiation load, may also be registered in accordance with this method, since many metabolic processes coexist with electro-biological and electro-chemical processes which result in resistance changes. A particular advantage is that these observations are derivable in a real time process. Further, parts of the body which are meant for transplanting can be examined in this way for their functional efficiency. By means of an XY position pick-off, yielding position signals signifying the position relative to the body to be measured, the distance between the body and the pick-up member can be taken into account by the computer device.

In order to eliminate the distance and movement effects between the pick-up element and the biological body and to be able to conduct topographic depth sensing, in accordance with the present invention, the primary field is formed with two frequencies, and in particular one low measuring frequency, and a frequency very high relative to the low frequency for elimination of surface effects, a part of the pick-up element being selectively tuned to this higher frequency and a part to the lower frequency and the measuring values generated in the pick-up elements being fed to a computer for separating the surface effects from the depth effects.

(a) Since changes in distance between the measuring apparatus and the body being scanned will, within certain limits, affect the high and low frequency fields to the same extent, compensation for distance variations can be achieved by comparing corresponding components of the high and low frequency fields and deriving the desired measurement signals from the difference therebetween.

(b) This difference is modulated by biological processes within the body only starting at a depth of penetration exceeding the depth of penetration of the higher frequency field.

(c) A topographic recording can thus be generated by scanning the body from different angles with a movable measuring device.

For forming the difference the computer device comprises an analog subtraction device in which the difference value is created by application of both measuring values with opposite phase and polarity. However, for arithmetic evaluation and storage it is practical to digitalize the measuring signals and to process the same by means of digital computers.

The construction of the arrangement is determined both by the part of the body to be measured and by the frequencies used. When higher frequencies are used (e.g., the transmitting elements are formed as a loop, in which a pick-up loop is centrally located. Between pick-up and transmitting loop at least one compensation element, also in the form of a loop, is provided.

In accordance with the present invention, the pick-up elements may also be constructed as spools, the compensation element being a spool coupled to, and surrounding the pick-up winding and excited by the primary current through phase shift elements and amplitude control elements. The primary control circuit preferably consists of a plurality of spools, which are coupled by ferrite cores which form a hollow body inside of which the pick-up element as well as the compensation device and the exciting spools are placed, the whole arrangement being surrounded by shielding.

This arrangement can, for example for recordings of the skull or measuring of the whole body, completely surround the latter and at the same time shield it from the outside so that external fields have little effect. For these measuring arrangements often not the absolute value but only the relative changes in the measured value by pulsation or other biological processes is of interest and the measured value is normalized by suppression of the carrier. In this embodiment, the primary carrier signal and the picked-up signal are applied to a product detector for deriving the amplitude, and a phase detector for deriving the phase angle of the desired measurement signal.

Functionally, the effect of the biological processes on the secondary field is to be considered a modulation. Thus, for complete supression of the carrier frequency, as happens with total compensation, only the sidebands remain. The product detector, which can also be constructed as a ring demodulator, allows sideband demodulation under simultaneous application of a new carrier portion from the primary field. An automatic control is supplied so that the control of the compensation need not be carried out by hand. For this purpose the measuring voltage is derived in accordance with the present invention via an amplifier from the pick-up element and this voltage, through an amplitude detector, controls an electronic amplitude control device and through a phase detector an electronic phase control device, the two control devices controlling the compensation devices. The measured amplitude value and the measured phase value are derived from the amplitude detector and the phase detector respectively, for recording. In accordance with the present invention the outputs of the demodulation device, the phase detector and the XY position take-off are provided with analog-digital converters, all three digital results being applied to storage and computer devices, means for graphic and pictorial display of the measuring results being connected thereto.

In accordance with the present invention, compensation for the primary field takes place only after demodulation of the measuring signal as well as of a compensation voltage which varies as a function of the primary field, by forming the difference of the demodulated signals. In this form of compensation, the amplifiers and the demodulation devices are included in the compensation. This measuring arrangement has the advantage that it requires only amplitude control. When measurements are to be conducted in real time processes, it is of advantage that the pick-up elements do not scan the field by means of actual movement, but that in accordance with the invention, a plurality of pick-up elements with compensation devices are mounted in a common transmitting element, the former being sequentially connected to the recording device by means of electronic switches.

For calibration of the apparatus, an amplitude modulation adjustable in degree of modulation and a phase modulation adjustable in degree of modulation are applied to the primary field for a short time, each with approximately the same order of magnitude as the biological happening. The absolute magnitudes of the resistance values as well as the phase shifts can then be derived by comparison with the calibrating modulation. Specifically, the degree of modulation is changed until the artifically superimposed modulation and the modulation resulting from the physiological happening are equally large. The amplitude of the artifical modulation then corresponds to the amplitude of the biological change. For this form of calibration not only the absolute values, but also percent changes and data in percent or in per thousand may be furnished.

The amplitude of the modulation values can however also be printed out or furnished in numerical values, the biological modulation being compared by means of a comparator with a step type calibration modulation. In this case the modulation value can be directly converted into a numerical value by means of an analog-digital converter and can be displayed or printed out.

The measuring of impedances has assumed a continually growing importance in medicine since such impedance measurements are more reliable than other presently known measurements in various fields, such as, for example, early detection of a number of different kinds of cancers.

New investigations have also shown that the life capacity of transplants can be estimated by means of impedance measurements.

A contactless measurement is not only of great importance for hygienic reasons, but also the start of death is, in accordance with new investigations, more exactly determinable by impedance measurements than by previous methods. Further advantages of the invention will be described in greater detail in the following with reference to the drawing which shows embodiments of the invention.

Figure 9:
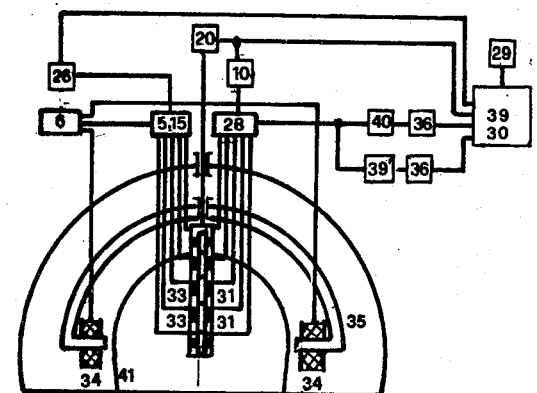
Figure 10:
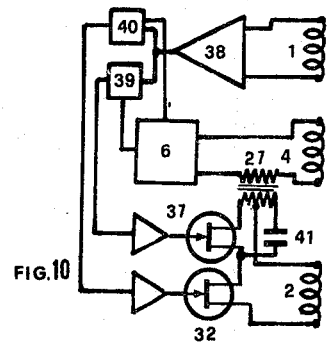
Figure 11:
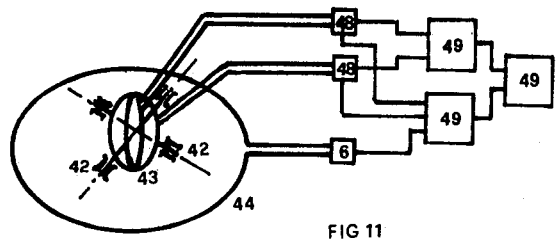
Figure 12:
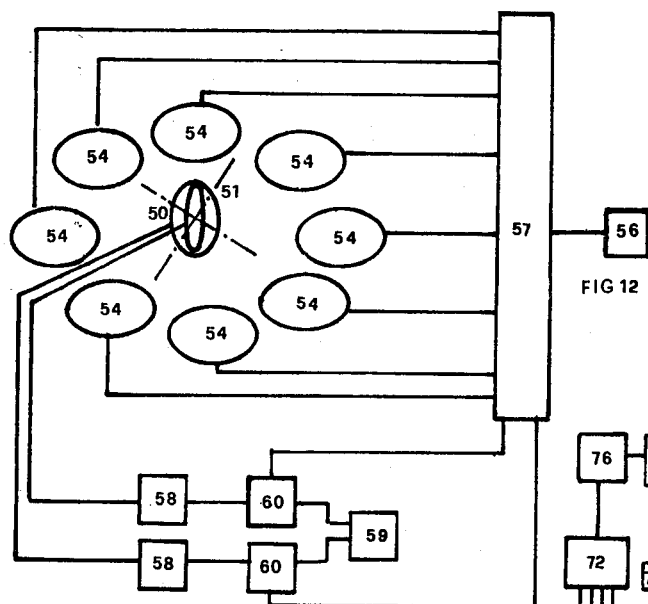
Figure 13:
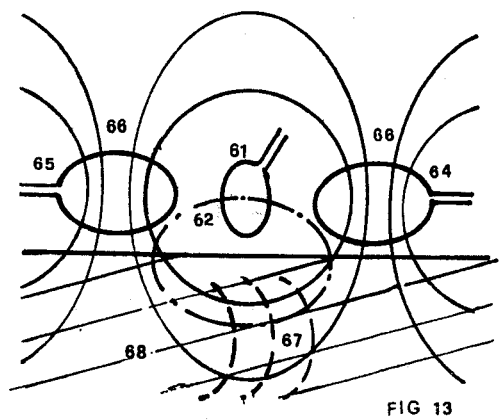
Figure 14:
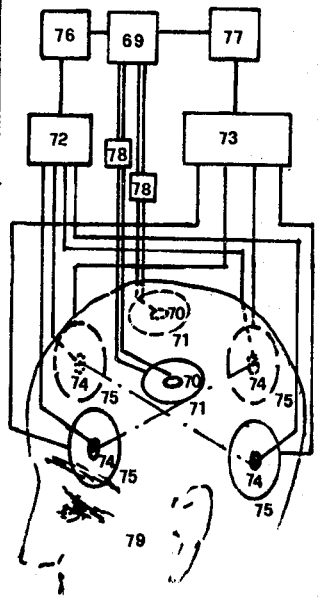
Figure 15:
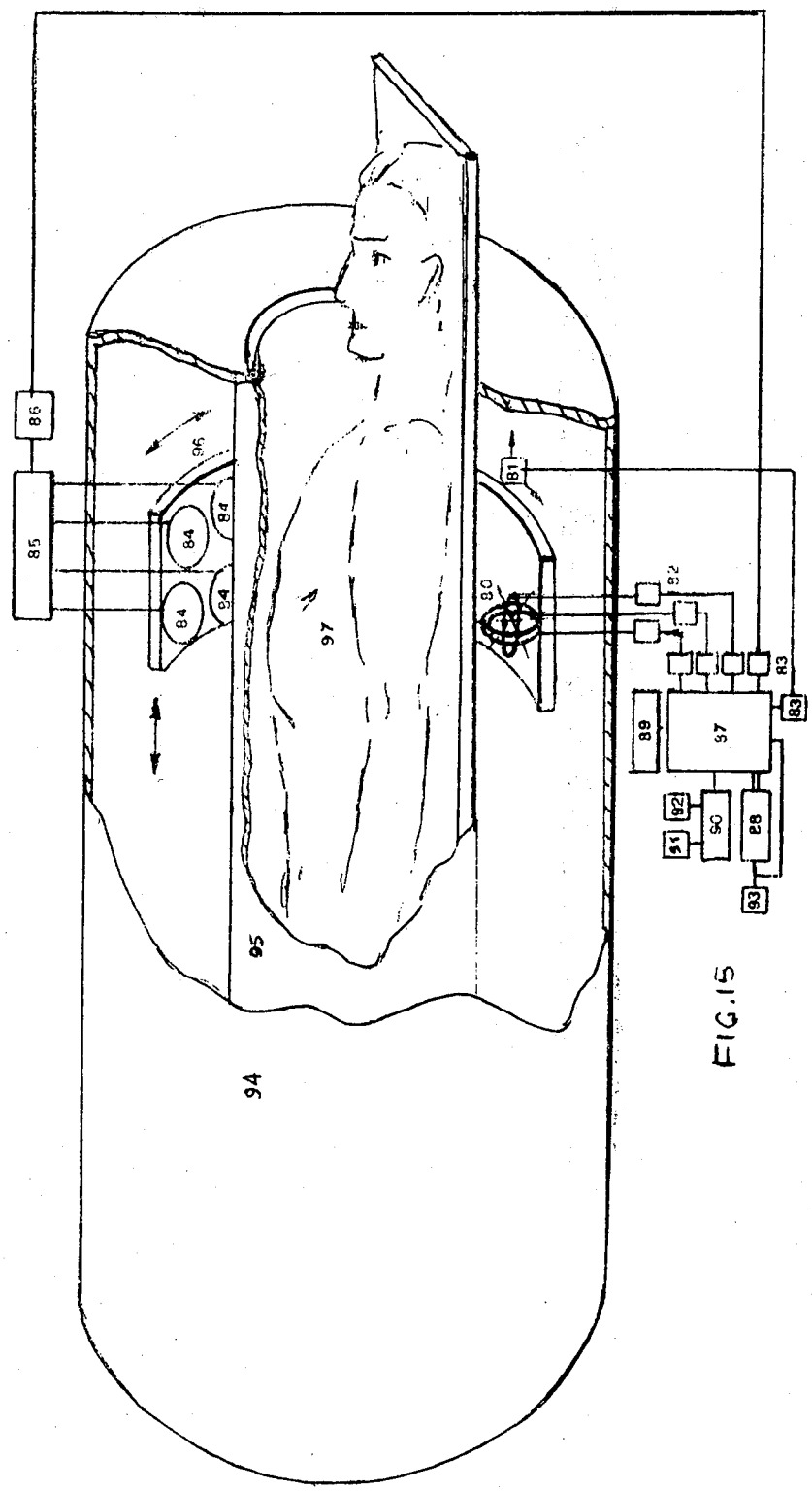

FIG. 9 shows an arrangement with several pick-off spools, which are scanned sequentially by means of an electronic switch, FIG. 10 shows an automatic compensation control circuit, FIG. 11 shows an arrangement with crossed pick-off elements, FIG. 12 shows a measuring arrangement with rotating field energization, FIG. 13 shows the field pattern with phase-shifted transmitting spools, FIG. 14 shows a measuring arrangement with two rotating field frequencies, FIG. 15 shows an arrangement for topographic recordings.

DESCRIPTION OF THE PREFERRED EMBODIMENTS

Figure 1:
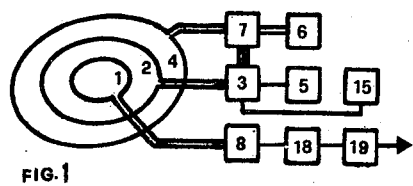
FIGS. 1, 2, 3 and 4 show preferred arrangements of the compensation device.

FIG. 1 shows a loop or spool-shaped pick-up element 1 that is connected through an amplifier 8 with a demodulator 18 and through a further amplifier 19 to a recorder for evaluation. A compensation element 2 is arranged around pick-up element 1 and lies within the transmitting element 4. The latter is energized by an alternating current generator 6 through a buffer circuit 7. The compensation element 2 is also energized by circuit 7, but through a compensation device 3 (described in greater detail with reference to FIG. 10) which allows the amplitude and phase of the energizing current to be varied by means of an amplitude control element 5 and a phase control element 15, respectively. For measuring purposes, controls 5 and 15 are adjusted so that no voltage is induced in pick-up element 1 when an electrically homogeneous reference body having substantially the same resistivity as the body to be measured is used. Signals induced in pick-up element 1 when the body on which measurements are to be conducted is substituted for the reference body are then considered measurement signals.

Figure 2:
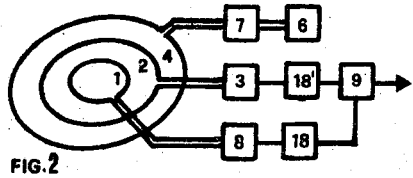

FIG. 2 shows an arrangement in which alternating current generator 6 energizes the transmitting element 4 through circuit 7, while the induced signal is derived from pick-up element 1 through amplifier 8 and demodulator 18 as was the case above. In the arrangement of FIG. 2, the voltage induced in the compensation element 2 by the primary field is applied to compensation device 3 and through demodulator 18' to an analogue computer 9. Analogue computer 9 also receives the signal at the output of demodulator 18, that is the signal generated by pick-up element 1. The difference between the two signals applied to analogue computer 9 constitutes the desired measurement signal. In this arrangement, compensation thus takes place only after demodulation.

Figure 3:
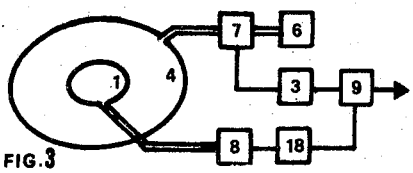

FIG. 3 shows an embodiment in which transmitting element 4 is energized from alternating current generator 6 through circuit 7 as in the above cases. However, here the output of circuit 7 is also applied to compensation device 3 and after demodulation is applied to one input of analogue computer 9. The voltage derived from pick-up element 1 is amplified by amplifier 8, demodulated by demodulator 18 and applied to the second input of analogue computer 9. Again, analogue computer 9 forms the difference between the two voltages applied thereto. This voltage is adjusted to be zero at the start of measurement. In the arrangement of FIG. 3, compensation is also carried out after demodulation. However, it is the advantage of the embodiment of FIG. 3 that only amplitude control of compensation is required. For a constant primary field, each change in the secondary field causes a change in the output value of analogue computer 9. The output value of analogue computer 9 thus corresponds to changes in the secondary field. In a preferred embodiment of the present invention analogue computer 9 is a difference amplifier.

Figure 4:
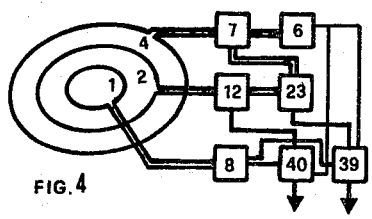

In the embodiment of FIG. 4, a field created by compensation element 2 directly compensates for the amplitude and phase of the primary field. Alternating current generator 6 generates low or high frequency oscillations which are applied through circuit 7 to transmitting element 4. The secondary field induces a voltage in pick-up element 1 which is amplified by amplifier 8. After amplification, the voltage is applied to a product detector 40 for amplitude demodulation and to a phase detector 39 for phase detection. The phase control voltage derived from phase detector 39 controls a phase control device 23 which in turn changes the phase of the compensation voltage derived from circuit 7. The compensation voltage, after phase correction, is applied to an amplitude control element 12. The amplitude of the voltage furnish by amplitude control element 12 is in turn controlled by the output of product 40. The output of control element 12, which has then been controlled both as to phase and amplitude, is applied to compensation element 2. The amplitude control element 12 and the phase control element 23 are so adjusted that the pick-up voltage which appears in pick-up element 1 is as small as possible. In this embodiment, the compensation voltage is controlled to correspond to secondary field changes in amplitude as well as phase. Thus, the control voltage appearing at the output of product detector 40 can be considered a measuring voltage for determining the amplitude of the secondary field strength, while the control voltage appearing at the output of phase detector 39 is a measure indicative of the phase of the secondary field. In this embodiment the amplitude as well as the phase of the secondary field are thus automatically indicated without additional adjustment. Control elements 12 and 23 are described in greater detail with reference to FIG. 10.

Figure 5:
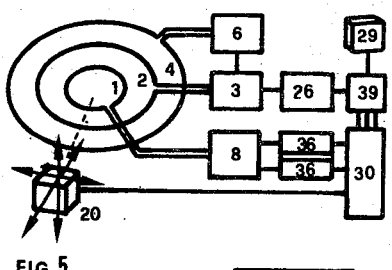
FIG. 5 shows a schematic representation with a position device, an analog-digital converter, storage-and computer device.

In FIG. 5, the alternating current generator 6 is directly connected to transmitting element 4 and is further connected to compensation device 3 whose output is coupled to compensation element 2. The voltage generated in pick-up element 1 is amplified in amplifier 8. The voltage furnished by amplifier 8 is digitalized by analogue/digital converters 36, in accordance with both phase and amplitude. The outputs of analogue/digital converters 36, are applied to a digital storage 30. A position signal furnishing device 20 is coupled to elements 1, 2 and 4 and furnishes a digital signal corresponding to the then-present position and distance between the measuring device and the object to be measured. This position signal is also applied to digital storage 30. A digital computer 39 controls a compensation control device 26, which in turn controls compensation device 3. The control is accomplished directly by digital computer 39, which is programmed to eliminate the effect of the primary field. Digital storage 30, digital computer 39, and a graphic display device 29 cooperate to generate sectional views from the stored individual values. The computer program is similar to that used in X-ray tomography. The object is scanned point-by-point, and for each point, its coordinates, the corresponding secondary field strength and the phase of the secondary field are stored in storage 30. Each so-found value is compared with the corresponding value previously stored for the reference body and the differences applied to display device 29. Different scanning frequencies and different reference bodies can be utilized to achieve specific displays. For example, circulatory examinations and examinations as to the compositions of the blood preferably use a measuring frequency of under 2 MHz. For frequencies less than 20 MHz, the resistivity of the blood changes as a function of the speed with which the blood is flowing. An unambiguous relationship exists between resistivity and the circulation of the blood as well as between resistivity and the number and condition of the erythrocytes. ("The physical principles of rheography" H. Rodler, from "Rheoencephalography and plethysmographical methods", Excerpta medica foundation Amsterdam 1969, page 49.) This effect is not detectable when measuring frequencies of over 2 MHz are used. The display can be in the form of field strength lines or light/dark values. Alternatively, display device 29 can be a color terminal, so that the computer results are keyed in color values and displays rich in contrast are achieved. This embodiment results in a substantially improved evaluation of the measured data.

Figure 6:
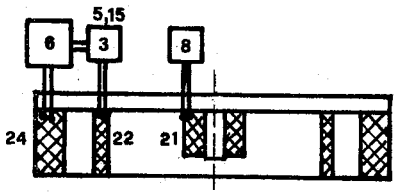
FIG. 6 shows an arrangement with spools.

In FIG. 6 the transmitting spool 24, is energized by an alternating current generator 6, which also energizes a compensation device 3. Regulators furnishing outputs 5 and 15 are associated with compensation device 3 which furnishes the energy required for compensation to compensation spool 22. The pick-up element is denoted by reference numeral 21. Its output is amplified by an amplifier 8 whose output furnishes an indication of the secondary field strength. This arrangement is particularly appropriate for spacially limited measurements in an exactly defined space. The enclosed space in this arrangement corresponds approximately to a hemisphere having the diameter of the outer transmitting spool 24. A corresponding area within the body can be scanned by applying the arrangement directly to the surface of the body at the appropriate location.

Figure 7:
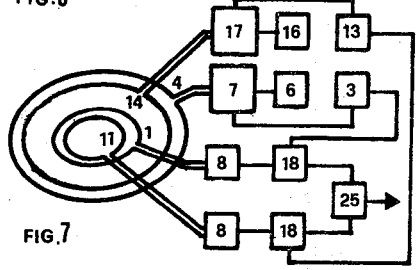
FIG. 7 shows the general arrangement using two frequencies.

FIG. 7 shows a measuring device wherein two frequencies are applied simultaneously. Here, alternating current generator 6 furnishes the lower frequency signal (e.g. 1–100 kHz) to circuit 7. The output of circuit 7 is applied to transmitting element 4 and also to compensation device 3. The output of pick-up element 1 is amplified by an amplifier 8 whose output is applied to a demodulator and difference amplifier 18. The latter forms the difference between the measuring voltage derived from pick-up element 1 and the compensation voltage for the lower frequencies derived from circuit 3. The alternating current generator furnishing the higher frequency (e.g. 10 to 100 MHz) signal is denoted by reference numeral 16. Its output is connected to a circuit 17 whose output is applied to a transmitting element 14 and a compensation device 13. The high frequency signal is picked up by a pick-up element 11 whose output is amplified in a amplifier 8'. The amplified output furnished by amplifier 8' is applied to a demodulator and difference amplifier 18' which furnishes a difference voltage corresponding to the difference between the voltage furnished by compensation device 13 and that furnished by pick-up element 11. The two difference voltages, that is, the lower and the higher frequency difference voltages, are applied to an analogue computer 25 which forms the difference between the two values. This difference is applied to the display device. In this arrangement both primary fields, that corresponding to the lower as well as that corresponding to the higher frequency, are compensated for by a compensation device after demodulation. The difference computed by analogue computer 25 corresponds to the difference of the results generated at the two frequencies. If the higher frequency signal is chosen to be high enough not to penetrate into the body, the higher frequency difference voltage varies as a function of distance to the body only so that the distance between the object to be measured and the pick-up device is automatically taken into consideration. Further, by correct choice of the corresponding frequency differences, the pick-up depth can be determined.

Figure 8:
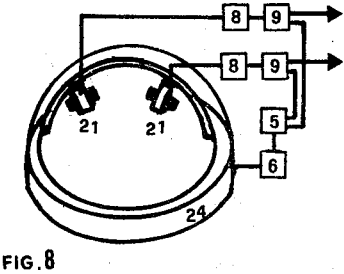
FIG. 8 shows an arrangement with spools and two pick-off elements.

FIG. 8 shows a measuring device with a transmitting spool 24 and pick-up spools 21, the axes of the latter being perpendicular to the axis of the former. The transmitting spool 24 is energized by alternating current generator 6. Alternating current generator 6 also furnishes the compensation energy which is applied through a control device 5 to analog computer 9 following demodulation.

Amplifiers 8 and 8' amplify and demodulate the voltage picked up by coils 21 and 21' respectively, so that two measured values are derived from the same field. Coils 21 and 21' may be rotatably mounted so that different components of the field (e.g. horizontal and vertical components) may be measured.

FIG. 9 shows a measuring device in which an alternating current generator 6 energizes two transmitting elements 34 which are coupled by a ferrite core 35. Several pick-up spools 31 are provided which may be switched into the circuit by electronic switches 28. Electronic switches 28 are in turn controlled by a switching device 10 which causes the pick-up spools 31 to be switched into the circuit sequentially in an order scanning the secondary field in a predetermined pattern. A compensation spool 33 is provided for each pick-up spool. Amplitude and phase control elements 5 and 15 are provided for the compensation spools. These are adjusted by a device 26 which in turn is controlled by a computer 39. The voltage picked up by the pick-up spools is applied to an amplitude product detector 40 and a phase detector 30'. Detectors 39' and 40 are each followed by an analog-digital converter 36 wherein the voltages are converted to digital signals. The digital signals are stored in a storage device 30, which is subject to access by a computer 39. A display 29 is associated with computer 39. A position signal furnishing device 20 also furnishes signals to storage 30. In this arrangement, as mentioned above the pick-up spools 31 are scanned sequentially by electronic switches 28 under control of the switching device 10. In an alternate embodiment, the plurality of pick-up spools 31 is replaced by a single spool and the whole arrangement is rotated so that the whole region to be examined is scanned. In the embodiment using a plurality of pick-up spools 31, the switching state of switches 28 also has to be entered into storage 30. The whole arrangement is surrounded by a shield 41, which comprises foil material arranged between the measuring device and the object to be measured and has slits for preventing the short-circuiting of windings.

FIG. 10 shows an arrangement for adjusting the phase and amplitude of the current in the compensation element. The pick-up element is again denoted by reference numeral 1, the transmitting element by reference numeral 4, the compensation element by reference numeral 2, and the alternating current generator by reference numeral 6. Alternating current generator 6 energizes transmitting element 4 through a current-voltage converter 27. For initial adjustment, the voltage picked up by pick-up element 1 is amplified in amplifier 38 and applied to a product detector 40 and a phase detector 39. The output of product detector 40 is applied to an amplifier to control the effective resistance of a field effect transistor 32. The amplitude of current flowing through compensation coil 2 varies as a function of the effective resistance of field effect transistor 32 i.e. field effect transistor 32 is an embodiment of control element 12 of FIG. 9. The output of phase detector 39 controls the resistance of a field effect transistor 37 which together with a capacitor 41 and the secondary winding of transformer 27 forms a phase bridge circuit, the phase angle of which is changed in accordance with the resistance of the field effect transistor 37. The bridge circuit constitutes phase control element 23 of FIG. 9. Thus by this arrangement the amplitude as well as the phase of the current in compensation element 2 is controlled.

FIG. 11 shows a transmitting element 44 and a pick-up element 43. Pick-up element 43 is a crossed spool, the two axes being adjustable in all directions by means of a movable bearing or by means of a spherical bearing 42. With this arrangement, total compensation of the primary field can be achieved. Amplifiers 48 and recording devices 49 are connected to the pick-up elements. Unit 6 is an alternating current generator.

In FIG. 12, eight transmitting elements 54 are shown. These are energized at different phase angles by phase shift circuits 57 which shift the output of an oscillator 56, so that a rotating field results. A reference phase angle corresponding to the then-present angle of the rotating field is applied by stage 5 to two phase detectors 60. Pick-up elements 50 and 51 are again crossed spools whose angular orientation is adjusted to compensate for the primary field as discussed with reference to FIG. 11, above. The output from each spool is passed through an amplifier 58 and phase detector 60 to a recording/evaluating device 59. Both phase and amplitude of the secondary field are recorded.

FIG. 13 schematically shows the field strength variation when two transmitting elements 64 and 65 are energized by currents 180° out of phase. The primary field 66 induces a secondary current 67 in object 68. Secondary current 67 in turn generates a secondary field 62 which is picked up by pick-up element 61. The same principle is also valid for arrangements with more than two phases. Primary field 66 is then compensated for appropriate positioning of the spools.

FIG. 14 shows an arrangement with four transmitting elements 74 for a lower frequency (e.g. 1–100 kHz) and four transmitting elements 75 for a high frequency (e.g. 10–100 MHz) respectively energized by signal generators 76 and 77 as distributed through networks 72 and 73. Two rotating fields with different velocity result, the secondary field of the lower frequency and that of the high frequency being picked up simultaneously in different locations by pick-up elements 70 and 71 respectively. The picked-up values are amplified by amplifiers 78 and evaluated by evaluation device 69 with respect to amplitude and phase. The display can be either in analog or digital form. The phase difference between the two rotating field vectors yields a new measuring parameter which, by appropriate choice of the difference frequency, can yield data regarding a biological process.

FIG. 15 shows a device for scanning the whole body by means of electromagnetic fields. Three pick-up elements 80 are furnished, whose axes are phase shifted by 90° relative to each other. Transmitting elements 84 are energized by oscillator 86 through a phase shifter 85 at one or a plurality of frequencies with four currents which are phase shifted relative to each other. Here the phase shift of the transmitting elements is so chosen that an axially bundled field results. This, after passing through the body, is picked up by three pick-up elements 80 amplified by three amplifiers 82, and, after analog-digital conversion in units 83, is applied to a digital computer 87. A read-write storage 88 is connected to computer 87, as is a program storage 89 and a tape storage 93. The transmitting and receiving elements are mounted on a rotatable and slidable device 96 so that they may be moved rythmically or continuously along and around the body. A position pick-off 81 supplies computer 87 with signals signifying the position of the scanning device. The computer evaluates the data supplied in accordance with the amplitude and phase shift of the secondary field as stored in storages 88 and 93 and the result is displayed as a sectional view under the control of program storage 89 through a peripheral unit 90 on color monitor 91. A printer 92 prints out the measured values. In this arrangement, the amplitude may be represented in light-dark values and the phase angle in color values or, by changing the frequency of the oscillator, different frequencies may be represented in different colors. It is also possible to represent particular biological processes as color values by corresponding programming. A shielding arrangement 94 shields the field from external effects. A magnetically conductive cylinder 95 is provided in which the patient 97 is enclosed. In this arrangement the compensation for the primary field can be achieved first by the positioning of pick-up element 80 and secondly by computer 87.

The compensation for the primary field component in the picked-up signal was carried out in the various embodiments by means of a reference body. As a specific example, a reference body made of salt water having an electrical resistivity of 300 ohm/cm and having the following dimensions: 200 mm diameter, 2 liters, was used.

Although the present invention has been described with reference to a plurality of particular embodiments, it is not to be limited to the circuits and structures shown, since many variations thereof will be evident to one skilled in the art are tended to be encompassed in the present invention as set forth in the following claims.

What is claimed is:

1. Apparatus for measuring physiological processes in a biological body, comprising, in combination, transmitting means for generating a primary electromagnetic field adapted to induce currents in said body, said currents creating a secondary field, said transmitting means comprising a plurality of spools coupled by a ferrite core forming a hollow body, and primary energizing means for energizing said transmitting spools; and pick-up means coupled to said secondary field for furnishing measurement signals indicative of the value of a predetermined characteristic of said secondary field, but substantially indepedent of said primary field, said pick-up means comprising display means for furnishing a display of said measurement signals; wherein said pick-up means comprises a pick-up spool located within said hollow body; and further comprising a compensation spool coupled to said pick-up spool and surrounding said pick-up spool, and phase shift means and amplitude control means for connecting said compensation to said primary energizing means.

2. Apparatus as set forth in claim 1, further comprising shielding surrounding said apparatus.

3. Apparatus as set forth in claim 1, wherein said measurement signals further comprise signals indicative of the phase angle of said secondary field.

4. Apparatus as set forth in claim 3, wherein said transmitting means comprises a plurality of transmitting elements, and energizing means for energizing each of said transmitting elements at a different frequency.

5. Apparatus as set forth in claim 4, further comprising means for adjusting the phase angle of said transmitting elements relative to each other, thereby allowing measurements to be conducted in a desired direction.

6. Apparatus for measuring physiological processes in a biological body, comprising, in combination, transmitting means for generating a primary electromagnetic field adapted to induce currents in said body said currents creating a secondary field, said transmitting means comprising a plurality of transmitting elements arranged along the perimeter of a circle and having axes arranged in a radial direction, and energizing means coupled to said transmitting elements for furnishing exciting currents phase shifted in correspondence to the angular position of the axes of said transmitting elements, thereby creating a rotation field; and pick-up means coupled to said secondary field for furnishing measurement signals indicative of the value of a predetermined characteristic of said secondary field, but substantially independent of said primary field, said pick-up means comprising display means for furnishing a display of said measurement signals; and wherein said pick-up means comprises at least a first and second pick-up spool having axes arranged at 90 degrees to each other for furnishing first and second pick-up signals respectively, means for adjusting the axes of said pick-up spools to substantially eliminate effects of said primary field on said first and second pick-up signals, and display means connected to said pick-up spools for furnishing a display of phase angle and amplitude of said secondary field in response to said first and second pick-up signals.

* * * * *